US012582756B2

(12) United States Patent
Koellhoffer et al.

(10) Patent No.: US 12,582,756 B2
(45) Date of Patent: *Mar. 24, 2026

(54) EXTRACORPOREAL OXYGENATOR WITH INTEGRATED AIR REMOVAL SYSTEM

(71) Applicant: Terumo Cardiovascular Systems Corporation, Ann Arbor, MI (US)

(72) Inventors: Stephen Koellhoffer, Lincoln University, PA (US); Eisuke Sasaki, Bear, DE (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 457 days.

This patent is subject to a terminal disclaimer.

(21) Appl. No.: 18/212,260

(22) Filed: Jun. 21, 2023

(65) Prior Publication Data

US 2023/0330312 A1 Oct. 19, 2023

Related U.S. Application Data

(63) Continuation of application No. 16/154,900, filed on Oct. 9, 2018, now Pat. No. 11,707,559.

(60) Provisional application No. 62/572,754, filed on Oct. 16, 2017.

(51) Int. Cl.
*A61M 1/16* (2006.01)
*A61M 1/36* (2006.01)

(52) U.S. Cl.
CPC ........ *A61M 1/1698* (2013.01); *A61M 1/1629* (2014.02); *A61M 1/3623* (2022.05); *A61M 1/3644* (2014.02)

(58) Field of Classification Search
CPC .... A61M 1/1698; A61M 1/1629; A61M 1/32; A61M 1/3623; A61M 1/3644
See application file for complete search history.

(56) References Cited

U.S. PATENT DOCUMENTS

| | | | |
|---|---|---|---|
| 4,698,207 A | 10/1987 | Bringham et al. | |
| 5,034,188 A | 7/1991 | Nakanishi et al. | |
| 5,120,501 A | 6/1992 | Mathewson et al. | |
| 6,117,390 A | 9/2000 | Corey, Jr. | |
| 6,302,860 B1 | 10/2001 | Gremel et al. | |

(Continued)

FOREIGN PATENT DOCUMENTS

| | | |
|---|---|---|
| CN | 103328019 | 9/2013 |
| CN | 103458938 | 12/2013 |

(Continued)

OTHER PUBLICATIONS

German Examination Report in German Appln. No. 102018217584.5, dated Jan. 26, 2023, 22 pages (with English translation).

(Continued)

*Primary Examiner* — Philip R Wiest
(74) *Attorney, Agent, or Firm* — Fish & Richardson P.C.

(57) ABSTRACT

Extracorporeal blood flow circuit devices can be used during medical procedures such as on-pump open-heart surgery. For example, extracorporeal heat exchange and oxygenation devices can be used to facilitate surgical procedures such as coronary artery bypass grafting. In some embodiments, such an oxygenation device can include an integrated air removal structure. In particular embodiments, the air removal structure can comprise one or more porous hollow fibers.

19 Claims, 8 Drawing Sheets

(56) References Cited

U.S. PATENT DOCUMENTS

| | | | |
|---|---|---|---|
| 6,524,267 | B1 | 2/2003 | Gremel et al. |
| 6,638,479 | B1 | 10/2003 | Elgas et al. |
| 6,998,093 | B1 | 2/2006 | McIntosh et al. |
| 7,749,435 | B2 | 7/2010 | Ogihara et al. |
| 7,762,976 | B2 | 7/2010 | Schreyer et al. |
| 8,318,092 | B2 | 11/2012 | Reggiani et al. |
| 8,388,566 | B2 | 3/2013 | Reggiani et al. |
| 8,518,259 | B2 | 8/2013 | Cloutier et al. |
| 8,529,834 | B2 | 9/2013 | Johns |
| 8,568,347 | B2 | 10/2013 | Brieske et al. |
| 8,574,309 | B2 | 11/2013 | Galea et al. |
| 8,585,969 | B2 | 11/2013 | Maianti et al. |
| 8,721,579 | B2 | 5/2014 | Müller-Spanka et al. |
| 8,834,399 | B2 | 9/2014 | Müller-Spanka et al. |
| 8,865,067 | B2 * | 10/2014 | Olson .................. B01D 63/025 |
| | | | 422/45 |
| 9,162,022 | B2 | 10/2015 | Reggiani et al. |
| 9,623,169 | B2 | 4/2017 | Arzt et al. |
| 11,707,559 | B2 * | 7/2023 | Koellhoffer ......... A61M 1/1629 |
| | | | 422/46 |
| 2006/0177343 | A1 | 8/2006 | Brian, III et al. |
| 2007/0166189 | A1 | 7/2007 | Ogihara |
| 2010/0114004 | A1 * | 5/2010 | Tanaka ................ A61M 1/1625 |
| | | | 604/6.13 |
| 2012/0193289 | A1 * | 8/2012 | Cloutier .............. A61M 1/1698 |
| | | | 422/46 |
| 2014/0050617 | A9 * | 2/2014 | Roller ................. A61M 1/3623 |
| | | | 422/46 |
| 2014/0216250 | A1 | 8/2014 | Meyer et al. |
| 2015/0231322 | A1 | 8/2015 | Spearman |
| 2016/0331882 | A1 | 11/2016 | Saito |
| 2016/0339163 | A1 | 11/2016 | Petralia et al. |
| 2016/0339164 | A1 | 11/2016 | Ochel et al. |
| 2017/0007755 | A1 | 1/2017 | Peticca et al. |
| 2017/0072123 | A1 | 3/2017 | Reggiani |
| 2017/0173244 | A1 * | 6/2017 | Saito ................... A61M 1/1621 |

FOREIGN PATENT DOCUMENTS

| | | |
|---|---|---|
| EP | 1624912 | 2/2006 |
| EP | 1713527 | 10/2006 |
| EP | 2540328 | 1/2013 |
| EP | 3100751 | 12/2016 |
| JP | H05042220 | 2/1993 |
| JP | H09201412 | 8/1997 |
| JP | 2003038904 | 2/2003 |
| JP | 2003111837 | 4/2003 |
| JP | 2008246141 | 10/2008 |
| JP | 2015506806 | 3/2015 |
| JP | 2016019666 | 2/2016 |
| JP | 2017136199 | 8/2017 |
| WO | WO 2004/101021 | 11/2004 |
| WO | WO 2005/067998 | 7/2005 |
| WO | WO 2015/046224 | 4/2015 |
| WO | WO 2015/115138 | 8/2015 |
| WO | WO 2017/051600 | 3/2017 |

OTHER PUBLICATIONS

German Office Action in German Appln. No. 102018217584.5, dated Oct. 29, 2019, 20 pages (with English translation).
German Patent and Trademark Office; Search Report in German Appln No. 19498-0029DE1 (Jul. 6, 2019), 13 pages.
Office Action in Chinese Appln. No. 201811195120.6, dated Sep. 2, 2022, 23 pages (with English translation).
Search Report in Japanese Appln. No. 2018-194374, dated Nov. 29, 2022, 38 pages (with English translation).
United Kingdom Intellectual Property Office; Search Report Mailed in corresponding British patent application No. GB1816191.9 (Mar. 21, 2019), 3 pages.

* cited by examiner

Priming Solution or Blood Inlet

Priming Solution or Blood Outlet

EXTRACORPOREAL OXYGENATOR WITH INTEGRATED AIR REMOVAL SYSTEM

CROSS-REFERENCE TO RELATED APPLICATIONS

This application is a continuation of U.S. application Ser. No. 16/154,900 filed Oct. 9, 2018, which claims the benefit of U.S. Provisional Application Ser. No. 62/572,754, filed Oct. 16, 2017. The disclosure of the prior applications are considered part of (and are incorporated by reference in) the disclosure of this application.

BACKGROUND

1. Technical Field

This document relates to devices used during surgical procedures for treatment of heart conditions. For example, this document relates to extracorporeal heat exchange and oxygenation devices that can be used for on-pump open-heart surgery to facilitate surgical procedures such as coronary artery bypass grafting. Some extracorporeal heat exchange and oxygenation devices described in this document include an integrated air removal structure.

2. Background Information

Hollow fiber oxygenators are utilized within the extracorporeal circuit to meet a patient's gas exchange needs during cardiopulmonary bypass surgery. Blood from the patient is either gravity drained, or VAVD (vacuum assisted venous drainage) is used to obtain the required amount of flow to maintain sufficient volume in a reservoir. A pump (e.g., a peristaltic pump or a centrifugal pump coupled with a magnetic driver) is used in the main line of the circuit in order to pump blood from the reservoir, through the oxygenator, and finally back to the patient.

Prior to the initiation of bypass, a crystalloid priming solution is pumped through the extracorporeal circuit to displace the air from the inside of the components of the circuit. In some cases, some amount of the air inside of the oxygenator may be difficult to remove during the priming procedure.

SUMMARY

This document describes devices used during surgical procedures for treatment of heart conditions. For example, this document describes extracorporeal heat exchange and oxygenation devices that can be used for on-pump open-heart surgery to facilitate surgical procedures such as coronary artery bypass grafting. Some extracorporeal heat exchange and oxygenation devices described herein can include an integrated air removal structure.

In one aspect, this disclosure is directed to a blood oxygenator apparatus that includes a blood inlet and a blood outlet. A blood flow path extends from the blood inlet to the blood outlet. The blood oxygenator apparatus also includes a gas exchange portion disposed along the blood flow path: a heat exchange portion disposed along the blood flow path prior to the gas exchange portion; and one or more porous hollow fibers disposed along the blood flow path prior to the heat exchange portion.

Such a blood oxygenator apparatus may optionally include one or more of the following features. An inside of the one or more porous hollow fibers may be communicative to an ambient space within or around the blood oxygenator apparatus. An inside of the one or more porous hollow fibers may be communicative to a vacuum source. The blood oxygenator may also include a flow distribution element disposed along the blood flow path prior to the one or more porous hollow fibers. In some embodiments, the one or more porous hollow fibers are wound around the flow distribution element. The one or more porous hollow fibers may be wound around the flow distribution element in a crisscrossing helical pattern. The one or more porous hollow fibers may be disposed around the flow distribution element in a non-crossing pattern. Pores of the one or more porous hollow fibers may allow air to enter an inside of the one or more porous hollow fibers while preventing liquid from entering the inside of the one or more porous hollow fibers.

In another aspect, this disclosure is directed to a blood oxygenator apparatus that includes: (i) a housing defining a blood inlet port and a blood outlet port: (ii) a heat exchanger disposed within the housing, the heat exchanger defining an internal space: (iii) a membrane oxygenator portion disposed within the housing, the oxygenator portion arranged concentrically around the heat exchanger; and (iv) one or more porous hollow fibers disposed within the internal space.

Such a blood oxygenator apparatus may optionally include one or more of the following features. The blood oxygenator apparatus may also include a flow distribution element disposed within the internal space. The one or more porous hollow fibers may be wound around the flow distribution element. The flow distribution element may be configured to facilitate a substantially uniform radial flow distribution of blood entering the heat exchanger. An inside of the one or more porous hollow fibers may be communicative to an ambient space within or around the blood oxygenator apparatus. An inside of the one or more porous hollow fibers may be communicative to a vacuum source. The one or more porous hollow fibers may be arranged in a crisscrossing pattern. The one or more porous hollow fibers may be arranged in a non-crossing pattern.

In another aspect, this disclosure is directed to a method of configuring a blood oxygenator apparatus. The method includes: disposing a membrane oxygenator within a housing that defines: (i) a blood inlet, (ii) a blood outlet, and (iii) a blood flow path extending from the blood inlet to the blood outlet: disposing a heat exchanger along the blood flow path prior to the membrane oxygenator; and disposing one or more porous hollow fibers along the blood flow path prior to the heat exchanger.

Such a method may optionally include one or more of the following features. The one or more porous hollow fibers may be arranged such that an inside of the one or more porous hollow fibers is communicative to an ambient space within or around the blood oxygenator apparatus. The method may also include configuring the oxygenator apparatus for connecting the one or more porous hollow fibers to a vacuum source. The method may also include disposing a flow distribution element along the blood flow path prior to the one or more porous hollow fibers. The one or more porous hollow fibers may be wound around the flow distribution element. The one or more porous hollow fibers may be wound around the flow distribution element in a crisscrossing helical pattern. At least some crisscrossed porous hollow fibers may be in fluid communication with each other by virtue of contact there between. The one or more porous hollow fibers may be disposed around the flow distribution element in a non-crossing pattern. Pores of the one or more porous hollow fibers may allow air to enter an inside of the one or more porous hollow fibers while preventing liquid from entering the inside of the one or more porous hollow fibers.

Particular embodiments of the subject matter described in this document can be implemented to realize one or more of the following advantages. In some embodiments, using the devices and methods provided herein, patients can undergo open-heart surgery with less potential for adverse effects. For example, using some embodiments described herein a patient will have a lessened exposure to the potential of receiving air emboli from the extracorporeal circuit. Hence, the risk of oxygen deprivation (e.g., stroke and other types of tissue ischemia) may be reduced. In addition, in some cases the time that clinicians spend priming the extracorporeal circuit to ensure that air within the circuit is sufficiently removed can be reduced. Accordingly, a less costly surgical procedure is possible, and the risks of clinician error can be reduced. Moreover, the use of some embodiments described herein can allow for the use of a simplified extracorporeal circuit in comparison to conventional extracorporeal circuits that employ additional air removal devices. Further, the air removal structure described herein facilitates the use of a low-prime oxygenator device. Such a low-prime device can result in less dilution of the patient's blood in comparison to conventional extracorporeal circuits. Because of less hemodilution, the potential for the patient's hematocrit to drop below a critical value is lessened, and the patient is therefore less likely to need a blood transfusion.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

that includes an integrated air removal structure, in accordance with some embodiments provided herein.

Figure 8:
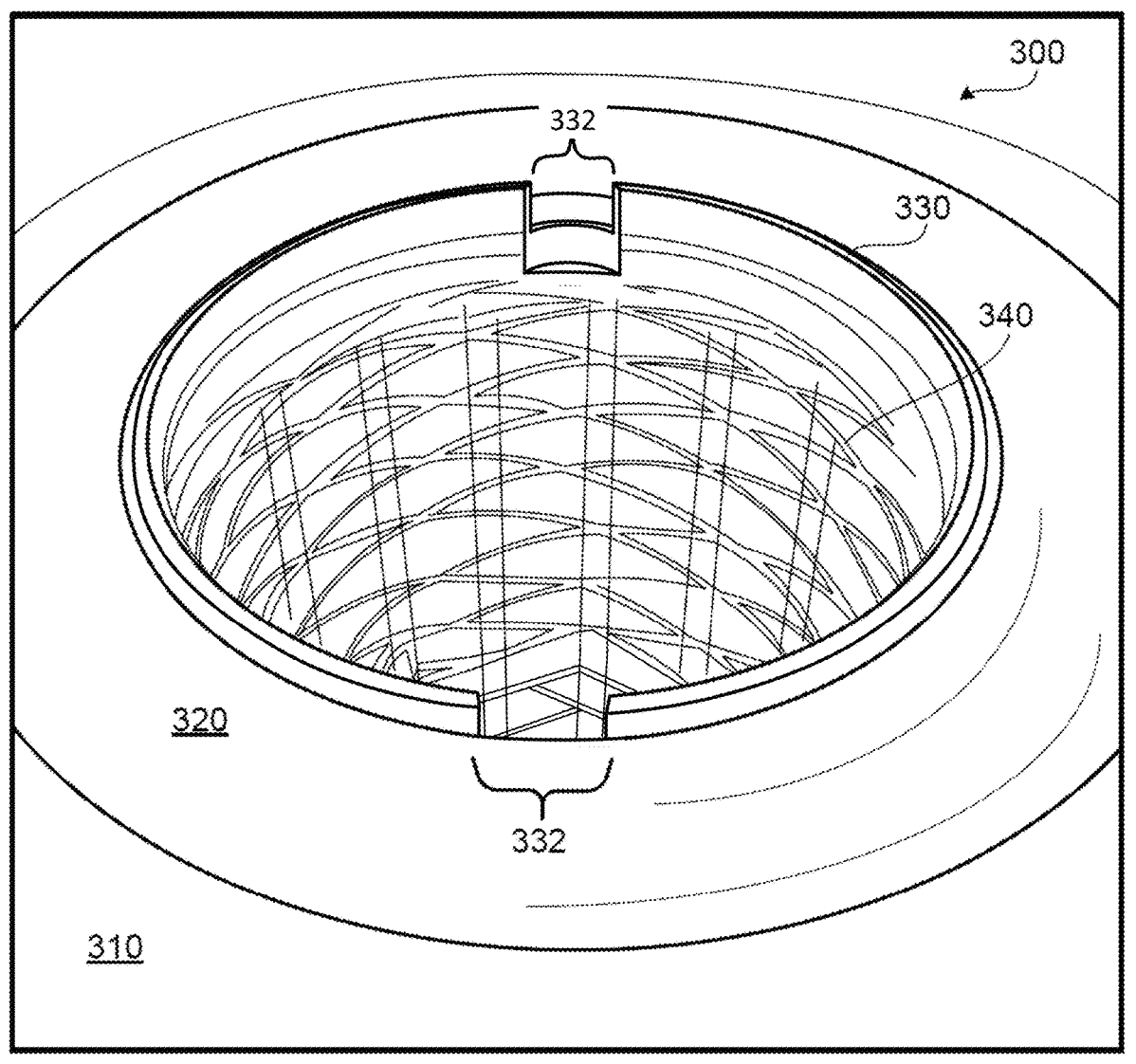

FIG. 8 is a perspective view of an end portion of an extracorporeal oxygenator (and integrated heat exchanger) that includes an integrated air removal structure, in accordance with some embodiments provided herein.

Like reference numbers represent corresponding parts throughout.

DETAILED DESCRIPTION

This document describes devices used during surgical procedures for treatment of heart conditions. For example, this document describes extracorporeal heat exchange and oxygenation devices that can be used for on-pump open-heart surgery to facilitate surgical procedures such as coronary artery bypass grafting. Some extracorporeal heat exchange and oxygenation devices described herein can include an integrated air removal structure.

Figure 1:
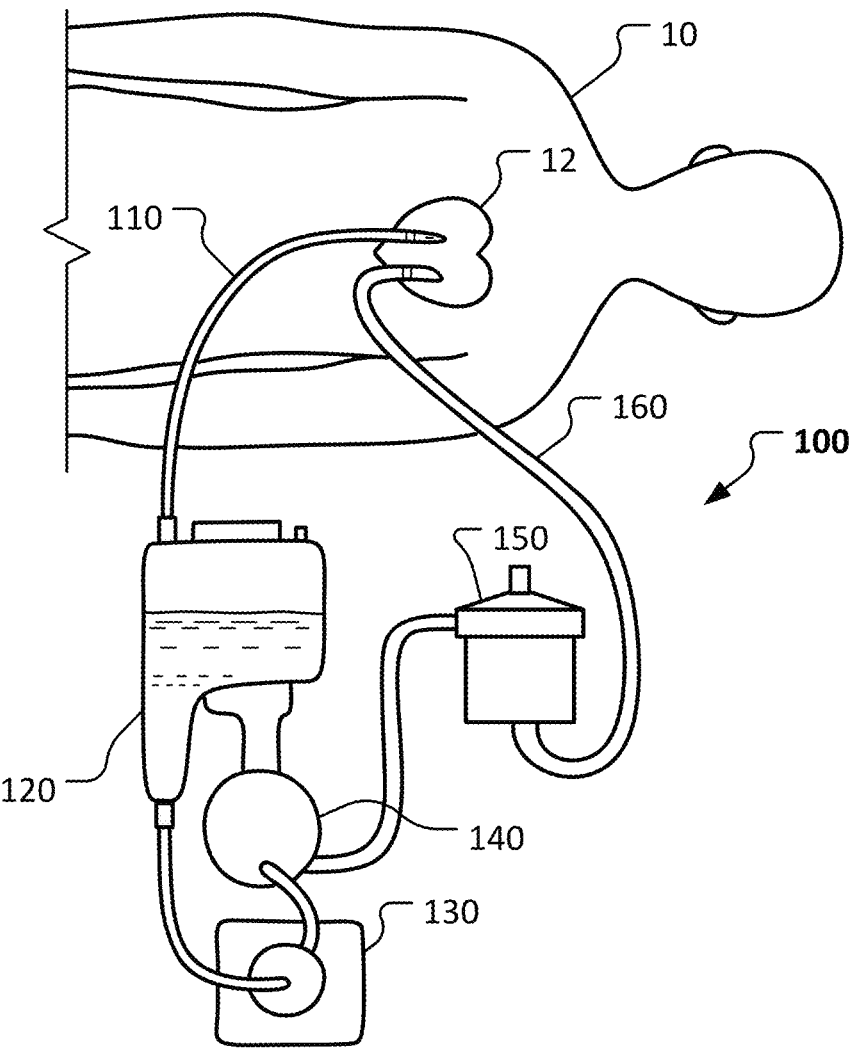
FIG. 1 is a schematic diagram of patient undergoing open-heart surgery while being supported using an extracorporeal circuit in accordance with some embodiments provided herein.

Referring to FIG. 1, a patient 10 can receive medical treatment while using an exemplary extracorporeal blood flow circuit 100. In this illustrative example, the patient 10 is undergoing a heart bypass procedure using the extracorporeal blood flow circuit 100. The circuit 100 is connected to the patient 10 at the patient's heart 12. Blood from the patient 10 is extracted from the patient 10 at the patient's heart 12; the blood is circulated through the circuit 100; and the blood is then returned to the patient's heart 12.

The example extracorporeal blood flow circuit 100 includes, at least, a venous tube 110, a blood reservoir 120, a pump 130, an oxygenator 140, an arterial filter 150, and an arterial tube 160. The venous tube 110 is in physical contact with the heart 12 and in fluid communication with the venous side of the circulatory system of the patient 10. The venous tube 110 is also in fluid communication with an inlet to the reservoir 120. An outlet from the reservoir 120 is connected by tubing to an inlet of the pump 130. The outlet of the pump 130 is connected to tubing to an inlet of the oxygenator 140. The outlet of the oxygenator 140 is connected by tubing to an inlet of the arterial filter 150. An outlet of the arterial filter 150 (which is optional) is connected to the arterial tube 160. The arterial tube 160 is in physical contact with the heart 12 and in fluid communication with the arterial side of the circulatory system of the patient 10.

Briefly, the extracorporeal blood flow circuit 100 operates by removing venous blood from the patient 10 via the venous tube 110. Blood from the venous tube 110 is deposited in the reservoir 120. At least some amount of blood is intended to be maintained in the reservoir 120 at all times during the medical procedure. Blood from the reservoir 120 is drawn from the reservoir 120 by the pump 130. The pressure generated by the pump 130 propels the blood through the oxygenator 140. In the oxygenator 140, the venous blood is enriched with oxygen. Additionally, in some cases the temperature of the blood can be selectively increased or decreased using a heat exchanger that is incorporated in the oxygenator 140. The oxygen-rich arterial blood exits the oxygenator 140, travels through the arterial filter 150, and is injected into the patient's heart 12 by the arterial tube 160.

One of skill in the art will recognize that, prior to use, the extracorporeal blood flow circuit 100 initially contains air that must be displaced before the circuit 100 can be connected to the patient 10. To displace the air within the circuit 100, a priming solution is introduced into the circuit 100. This process is called priming the circuit 100.

Figure 2:
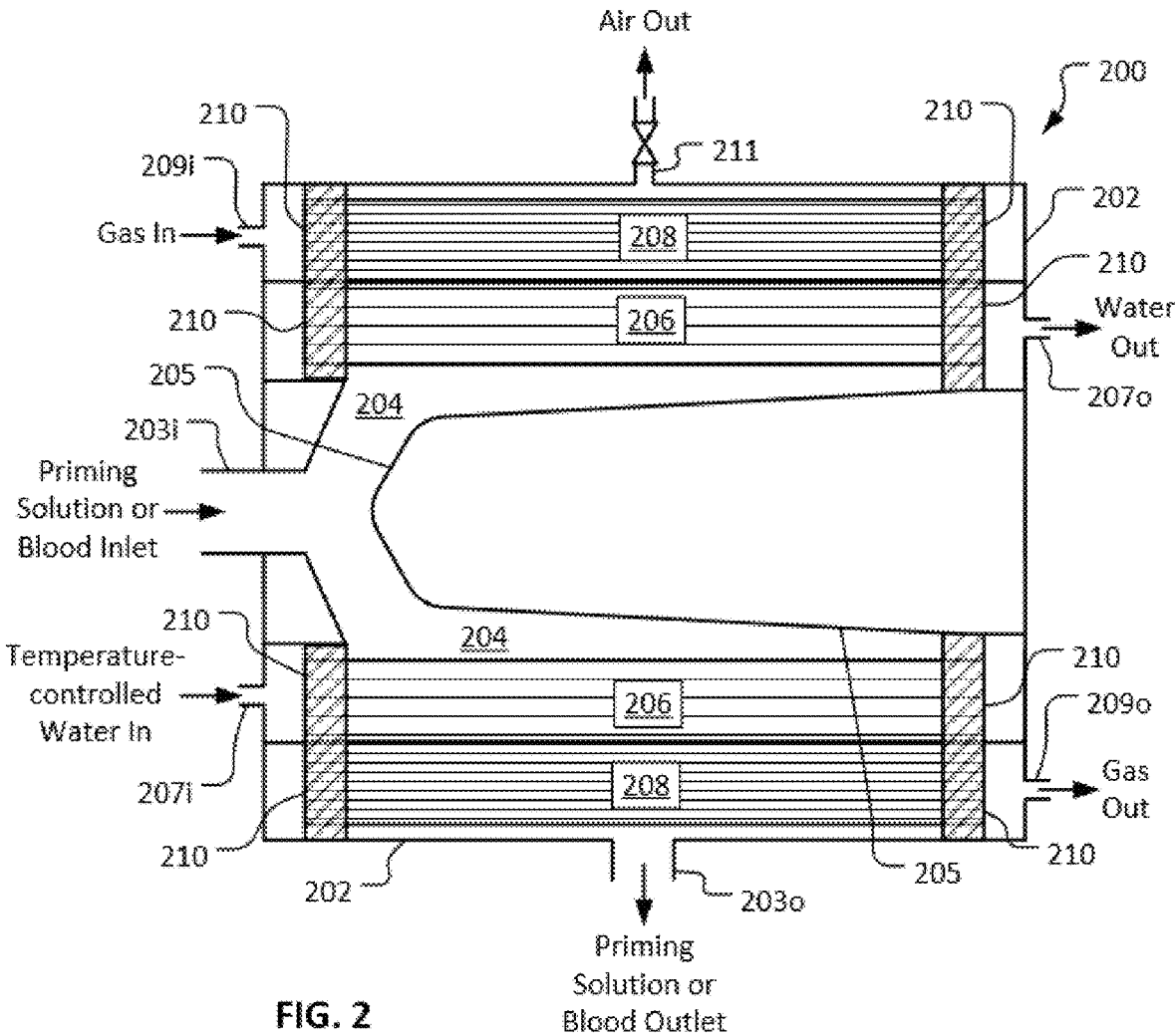
FIG. 2 is schematic depiction of an extracorporeal oxygenator (and integrated heat exchanger), in accordance with some embodiments provided herein.

Referring to FIG. 2, an example oxygenator with an integrated heat exchanger 200 (or simply "oxygenator 200") is schematically depicted. The oxygenator 200 includes a housing 202. The housing 202 defines an inlet port 203*i* and an outlet port 2030. A blood flow path extends from the inlet port 203*i* to the outlet port 2030.

A heat exchanger 206 is disposed along the blood flow path. As blood (or priming solution) enters the housing 202 through the inlet port 203*i*, the blood flows generally radially towards the heat exchanger 206, and continues to flow radially into the heat exchanger 206. Temperature-controlled water is also passed through the heat exchanger 206, from an inlet port 207*i* to an outlet port 2070 (or in the opposite direction). While the heat exchanger 206 allows heat to transfer between the temperature-controlled water and the blood, the wall(s) of the heat exchanger 206 physically separate the temperature-controlled water from the blood (to prevent mixing) in the typical fashion of a heat exchanger. The heat exchanger 206 can be constructed of metallic or polymeric materials. In some embodiments, the heat exchanger 206 is constructed of multiple small tubes. An internal space 204 is defined by the heat exchanger 206. Incoming blood flows through the internal space 204 prior to reaching the heat exchanger 206.

In some embodiments, a flow distribution element 205 is disposed within the internal space 204. The flow distribution element 205 is configured to facilitate a substantially uniform radial flow distribution of blood as it enters the internal space 204 and transitions to entering the heat exchanger 206.

An oxygenator portion 208 (which can also be referred to as a "gas exchange portion") is disposed within the housing 202 along the blood flow path after the heat exchanger 206. In some embodiments, the oxygenator portion 208 is arranged concentrically around the heat exchanger 206 such that blood flowing radially through the heat exchanger 206 can continue flowing radially through the oxygenator portion 208. Gases are also passed through the oxygenator portion 208, from an inlet port 209*i* to an outlet port 2090. The oxygenator portion 208 can be constructed of hollow fibers (membranes) that allow gas transfer (e.g., exchanges of oxygen and carbon dioxide) between the gases and the blood while preventing direct mixing of the gas and the blood.

In some embodiments, the ends of the individual tubular elements of the heat exchanger 206 and/or the oxygenator portion 208 are physically bound together using a potting material 210. The potting material 210 can be urethane in some cases. After the potting material 210 (in a flowable state) is applied to the ends of the individual tubular elements of the heat exchanger 206 and/or the oxygenator portion 208, the potting material 210 is allowed to solidify. In the solid state, the potting material 210 (encasing the ends of the individual tubular elements of the heat exchanger 206 and/or the oxygenator portion 208) is sheared. In doing so, openings to the insides of the individual tubular elements of the heat exchanger 206 and/or the oxygenator portion 208 are exposed. Those openings allow the temperature-controlled water to flow into the inside of the tubular elements of the heat exchanger 206, and the gases to flow into the inside of the tubular elements of the oxygenator portion 208.

After the blood flows through the oxygenator portion 208 (and an optional filter media in some embodiments), it continues flowing radially outward until it encounters the wall of the housing 202. Then, the blood flows out of the outlet port 2030. A purge port 211 can also be included. The purge port 211 can be used, for example, to allow air to exit from within the housing 202 while a liquid (e.g., a priming solution or blood) is entering the housing 202. Thereafter, the purge port 211 can be closed.

Figure 3:
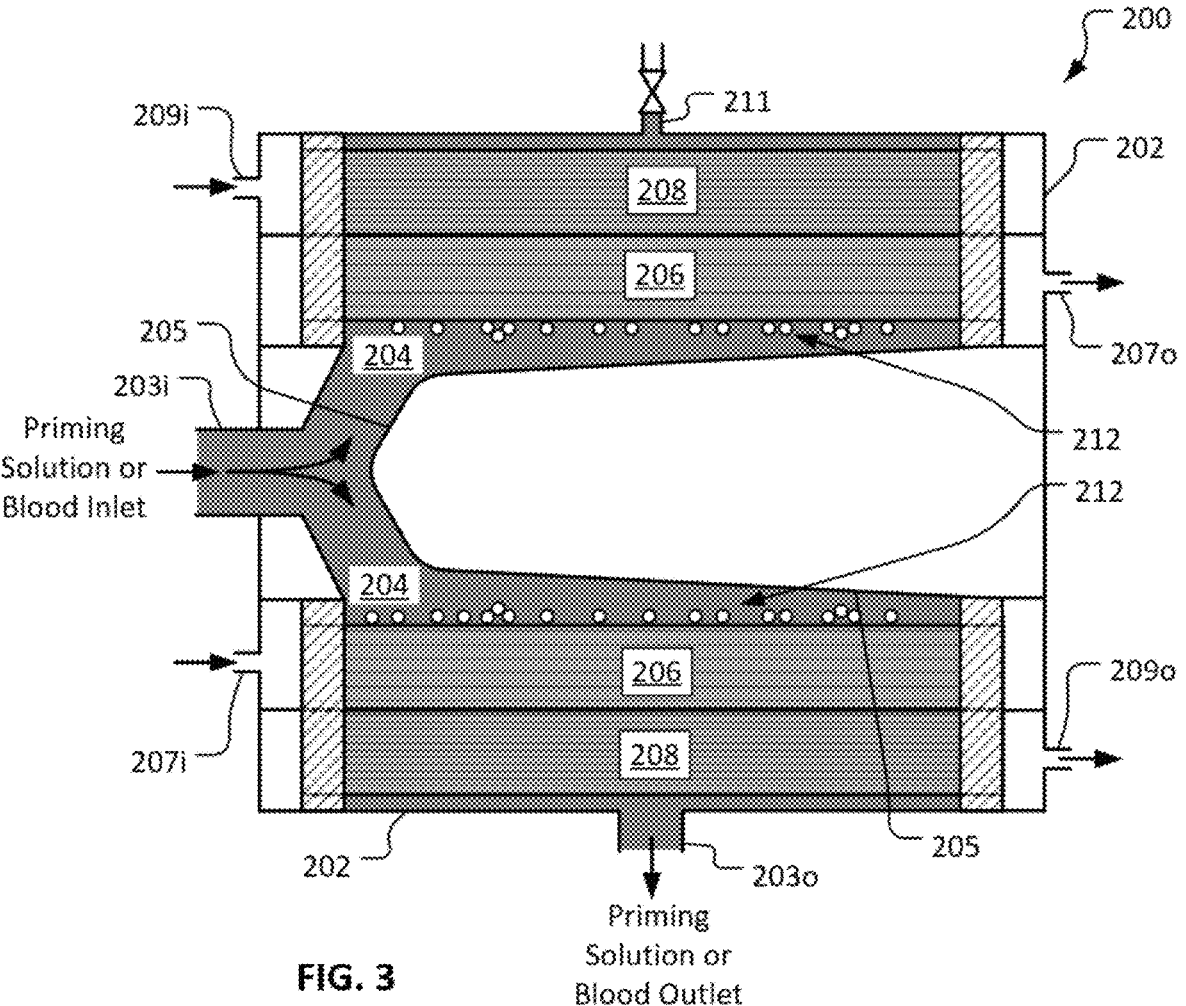
FIG. 3 schematically depicts a priming process of the extracorporeal oxygenator of FIG. 2.

FIG. 3 illustrates a priming process of the oxygenator 200. A priming solution is pumped into the housing 202 through the inlet port 203*i*. The priming solution enters the internal space 204 where it may impinge on flow distribution element 205. Then the priming solution flows generally radially into the heat exchanger 206. From the heat exchanger 206, the priming solution flows generally radially into the oxygenator portion 208. After passing through the oxygenator portion 208, the priming solution fills the remainder of the space within the housing 202, and then exits the oxygenator 200 through the outlet port 2030.

As the priming solution flows in the manner described above, air within the housing 202 is displaced by the priming solution. At least some of the displaced air can be allow to exit the housing through the purge port 211. When priming solution begins to emerge through the purge port 211, the purge port 211 can be closed. At that point, the clinician can rightly assume that the majority of the air previously within the housing 202 has been eliminated. That said, some small bubbles or pockets of air may still be present within the housing 202.

In some cases, small bubbles of air 212 may at least initially tend to remain near the entrance to the heat exchanger 206. If the priming solution is allowed to continue flowing, after a period of time, most or all of the small bubbles of air 212 may eventually flow out of the housing 202. In some cases, however, some of the small bubbles of air 212 may remain, or the clinician may prefer to not prime for a long enough time for the all of the small bubbles of air 212 to flow out of the housing 202.

Figure 4:
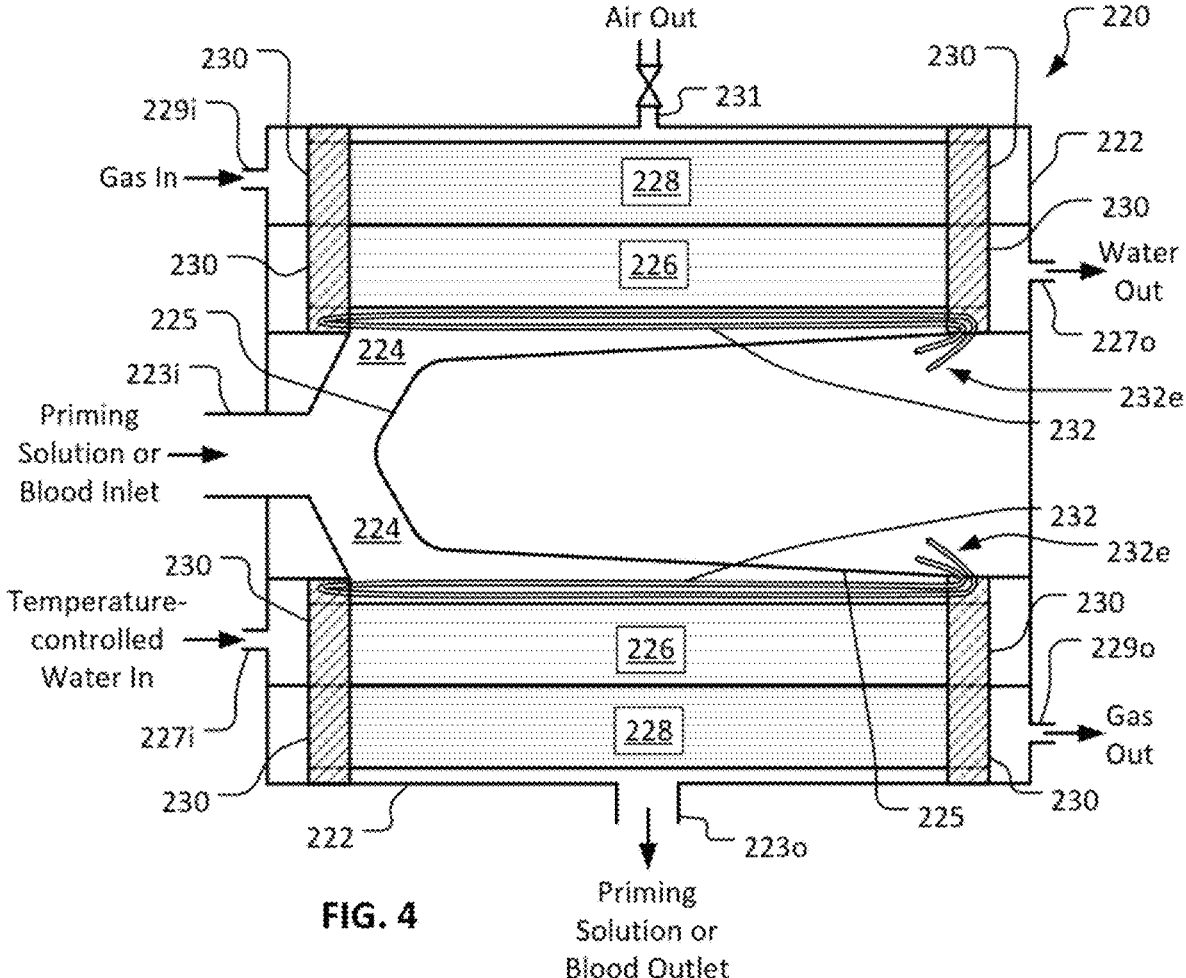
FIG. 4 is schematic depiction of an extracorporeal oxygenator (and integrated heat exchanger) that includes an integrated air removal structure, in accordance with some embodiments provided herein.

Referring to FIG. 4, an example oxygenator with an integrated heat exchanger 220 (or simply "oxygenator 220") is schematically depicted. The oxygenator 220 includes a housing 222. The housing 222 defines an inlet port 223*i* and an outlet port 2230. A blood flow path extends from the inlet port 223*i* to the outlet port 2230.

A heat exchanger 226 is disposed along the blood flow path. As blood (or priming solution) enters the housing 222 through the inlet port 223*i*, the blood flows generally radially towards the heat exchanger 226, and continues to flow radially into the heat exchanger 226. Temperature-controlled water is also passed through the heat exchanger 226, from an inlet port 227*i* to an outlet port 2270. While the heat exchanger 226 allows heat to transfer between the temperature-controlled water and the blood, the wall(s) of the heat exchanger 226 physically separate the temperature-controlled water from the blood (to prevent mixing) in the typical fashion of a heat exchanger. The heat exchanger 226 can be constructed of metallic and/or polymeric materials. In some embodiments, the heat exchanger 226 is constructed of multiple small tubes. An internal space 224 is defined by the heat exchanger 226. Incoming blood flows through the internal space 224 prior to reaching the heat exchanger 226.

In some embodiments, such as the depicted embodiment, a flow distribution element 225 is disposed within the internal space 224. The flow distribution element 225 is configured to facilitate a substantially uniform radial flow distribution of blood as it enters the internal space 224 and transitions to entering the heat exchanger 226.

An oxygenator portion 228 (which can also be referred to as a "gas exchange portion") is disposed within the housing 222 along the blood flow path after the heat exchanger 226. In some embodiments, the oxygenator portion 228 is arranged concentrically around the heat exchanger 226 such that blood flowing radially through the heat exchanger 226 can continue flowing radially through the oxygenator portion 228. Gases are also passed through the oxygenator portion 228, from an inlet port 229i to an outlet port 2290. The oxygenator portion 228 can be constructed of hollow fibers (membranes) that allow gas transfer (e.g., exchanges of oxygen and carbon dioxide) between the gases and the blood while preventing direct mixing of the gas and the blood.

The ends of the individual tubular elements of the heat exchanger 226 and/or the oxygenator portion 228 can be physically bound together using a potting material 230 as described above in reference to the oxygenator 200. A purge port 231 can also be included. In some embodiments, an optional arterial filter media is also included within the oxygenator 220.

Additionally, the oxygenator 220 includes one or more porous hollow fibers 232. In the depicted embodiment, the one or more porous hollow fibers 232 are disposed within the internal space 224 along the blood flow path prior to the heat exchanger 226. In some embodiments, the one or more porous hollow fibers 232 are disposed within the interior of the heat exchanger 226. That is, in some embodiments the one or more porous hollow fibers 232 are interspersed with the physical material(s) (e.g., tubes, etc.) of the heat exchanger 226. In particular embodiments, the one or more porous hollow fibers 232 are disposed both within the internal space 224 along the blood flow path prior to the heat exchanger 226 and within the interior of the heat exchanger 226.

In some embodiments, the one or more porous hollow fibers 232 are made of polypropylene fiber. In particular embodiments, the diameter of the one or more porous hollow fibers 232 can be about 170 μm, or about 300 μm, or any other suitable size. The one or more porous hollow fibers 232 have pores that are sized to allow air to enter an inside of the one or more porous hollow fibers 232 while preventing liquid from entering the inside of the one or more porous hollow fibers 232. Accordingly, the one or more porous hollow fibers 232 can help to remove air from within the internal space 224. The hydrostatic pressure of the priming solution (or blood) and the dynamic pressure (from flow momentum) can each provide driving force for the air to enter the one or more porous hollow fibers 232.

The one or more porous hollow fibers 232 have free ends 232e that are open ends. In the depicted embodiment, the free ends 232e are located at an ambient space within or around the blood oxygenator 220. Accordingly, an inside of the one or more porous hollow fibers 232 is fluidly communicative to the ambient space within or around the blood oxygenator apparatus 220. That is, air entering the one or more porous hollow fibers 232 can exit from the free ends 232e to the ambient space within or around the blood oxygenator apparatus 220. In some embodiments, the free ends 232e are located to vent into the same space as the oxygenator portion 228. That is, air entering the one or more porous hollow fibers 232 can exit from the free ends 232e to the same space as the oxygenator portion 228 and exit the oxygenator 220 from the gas outlet port 2290.

In some embodiments, the free ends 232e are connected to a vacuum source (not shown). Accordingly, the use of the vacuum source may result in a greater pressure differential (driving force) to facilitate removal of air in an enhanced manner (as compared to simply venting the one or more porous hollow fibers 232 to the ambient atmosphere).

In some embodiments, the one or more porous hollow fibers 232 can be physically bound to the other portions of the oxygenator 220 using (at least partially) the potting material 230. In the depicted embodiment, unlike the heat exchanger 226 and the oxygenator portion 228, the ends of the one or more porous hollow fibers 232 are not exposed by the shearing of the potting material 230 (because the free ends 232e are already exposed to the ambient atmosphere). Alternatively, or additionally, in some embodiments ends of one or more portions (or entirely) are exposed as a result of shearing or otherwise removing some of the potting material 230.

Figure 5:
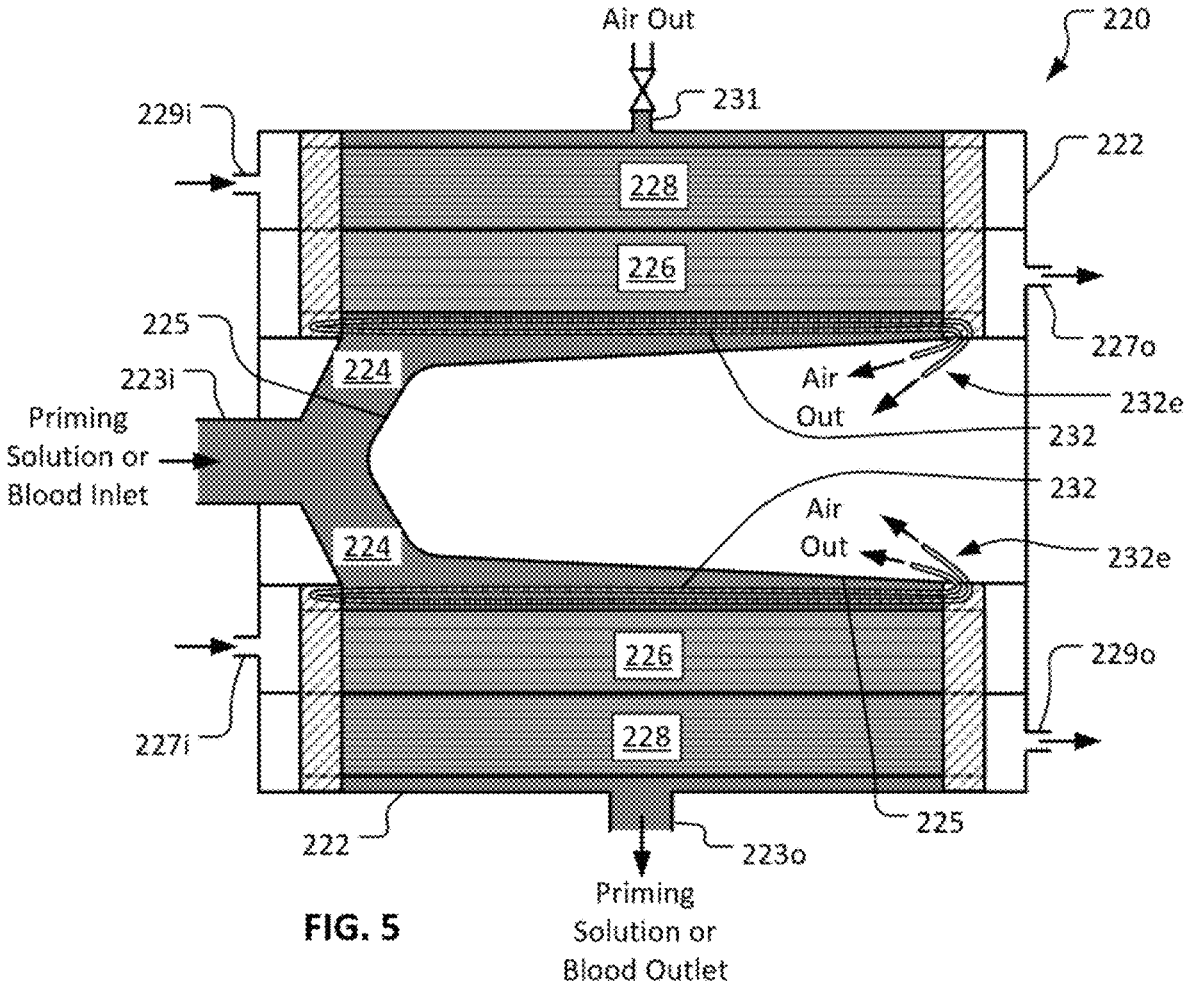
FIG. 5 schematically depicts a priming process of the extracorporeal oxygenator of FIG. 4.

FIG. 5 illustrates a priming process of the oxygenator 220. A priming solution is pumped into the housing 222 through the inlet port 223i. The priming solution enters the internal space 224 where it may impinge on flow distribution element 225. Then the priming solution flows generally radially into the heat exchanger 226. From the heat exchanger 226, the priming solution flows generally radially into the oxygenator portion 228. After passing through the oxygenator portion 228, the priming solution fills the remainder of the space within the housing 222, and then exits the oxygenator 220 through the outlet port 2230.

As the priming solution flows in the manner described above, air within the housing 222 is displaced by the priming solution. At least some of the displaced air can be allowed to exit the housing through the purge port 231. When priming solution begins to emerge through the purge port 231, the purge port 231 can be closed. At that point, the clinician can rightly assume that the majority of the air previously within the housing 222 has been eliminated. That said, some small bubbles or pockets of air may still be present within the housing 222.

In the depicted embodiment, the oxygenator 220 includes the one or more porous hollow fibers 232. Accordingly, if some small bubbles or pockets of air are still present within the housing 222, the air will tend to enter into the one or more porous hollow fibers 232. After entering the one or more porous hollow fibers 232, the air will flow out of the one or more porous hollow fibers 232 via the free ends 232e and into the ambient space within or around the blood oxygenator apparatus 220. In this fashion, the one or more porous hollow fibers 232 expedites the removal of air within the oxygenator 220 during the priming process. Additionally, if air is or becomes entrained in the blood circulating during the medical procedure that uses the oxygenator 220, the one or more porous hollow fibers 232 can serve to help remove such air.

Figure 6:
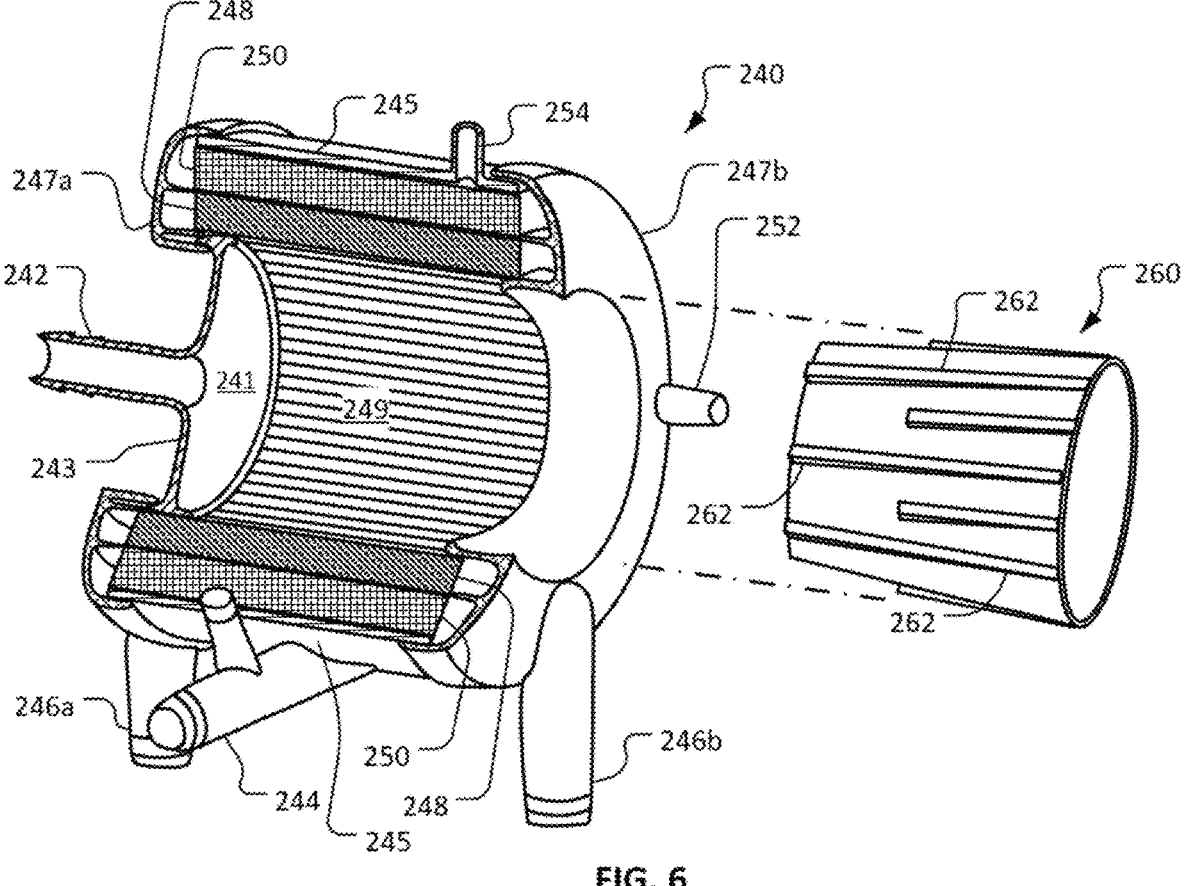
FIG. 6 is an exploded, cut-away perspective view of an extracorporeal oxygenator (and integrated heat exchanger).

Referring to FIG. 6, an example oxygenator 240 (including an integrated heat exchanger) is shown in an exploded, cut-away perspective view. The oxygenator 240 includes a blood inlet 242 extending from an end wall 243, and a blood outlet 244 extending from a peripheral housing 245. As the blood flows between the blood inlet 242 and the blood outlet 244, the blood passes through a heat exchanger 248 and an oxygenator fiber bundle 250. In some embodiments, one or more filter members may also be included in the blood flow path within the oxygenator module 240. The heat exchanger 248 defines the interior space 241.

In some embodiments, an optional flow distribution element 249 may be included in the oxygenator module 240. The flow distribution element 249 can facilitate a desired flow distribution (e.g., a substantially uniform radial flow distribution in some embodiments) of blood as the blood passes from the interior space 241 to the heat exchanger 248.

The oxygenator 240 also includes a first water port 246a and a second water port 246b. The water ports 246a and 246b allow the inflow and outflow of water for cooling or heating the blood via the heat exchanger 248. The oxygenator 240 also includes a gas inlet (not visible) and a gas outlet 252. The gas inlet and outlet 252 allow the inflow and outflow of oxygen-rich gas for oxygenating the blood via the oxygenator fiber bundle 250. The oxygenator 240 includes two end caps 247*a* and 247*b* that help structurally hold the parts of the oxygenator module 240 together, and that define annular manifolds for the water and oxygen-rich gas. The oxygenator 240 also includes other parts such as a purge port 254, and other various parts and features known to one of skill in the art.

In the depicted embodiment, the oxygenator 240 also includes an optional flow distribution element 260 (which also may be referred to as a "heat exchanger body") that is disposed within the internal space 241. Accordingly, the flow distribution element 260 can facilitate blood flowing into the internal space 241 to flow in a substantially uniform radial flow pattern thereafter. The flow distribution element 260 can have a frustoconical shape. In some embodiments, the flow distribution element 260 includes one or more ribs 262. The ribs 262 can be shaped and oriented on the outer surface of the other portions of the flow distribution element 260 allow blood flowing into the internal space 241 to substantially fill the internal space 241 before flowing in a substantially uniform radial flow pattern thereafter.

Figure 7:
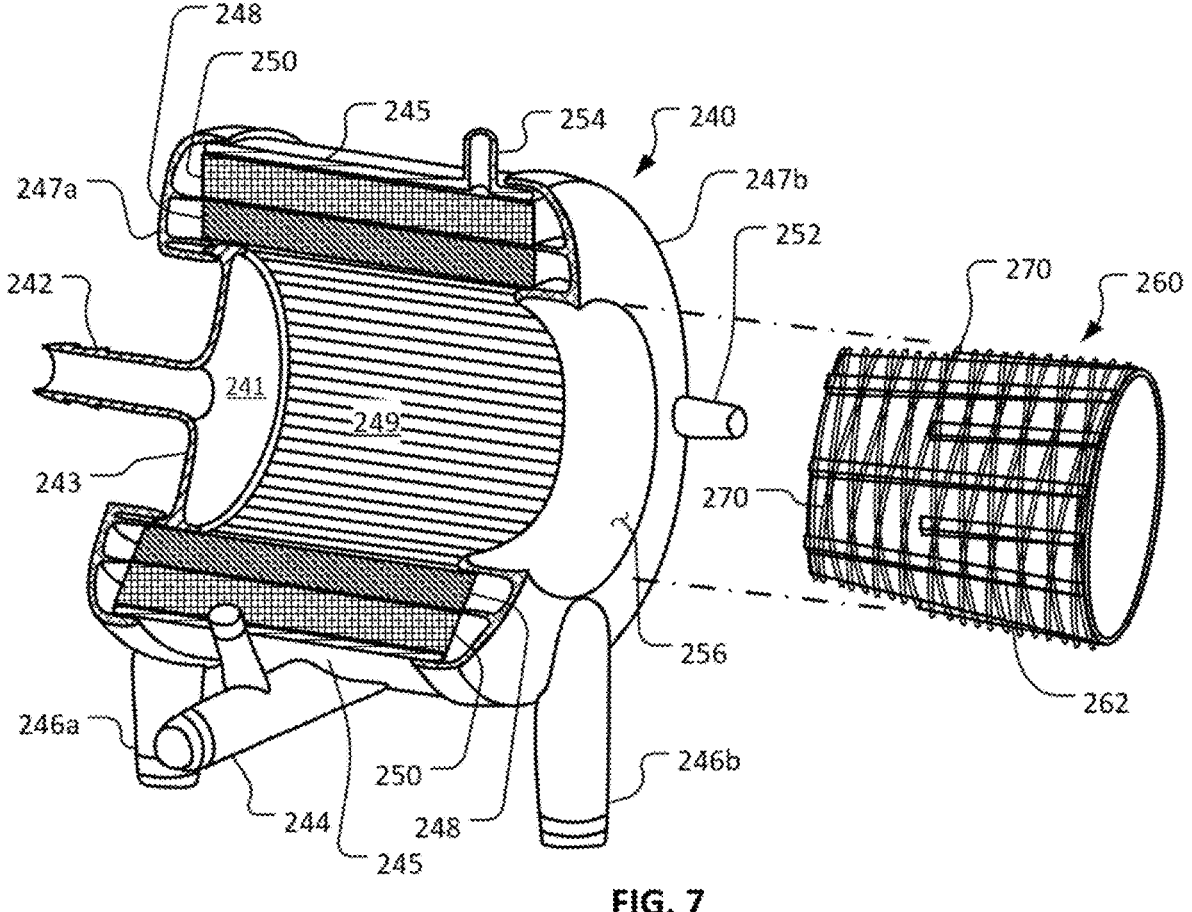
FIG. 7 is an exploded, cut-away perspective view of an extracorporeal oxygenator (and integrated heat exchanger)

Referring to FIG. 7, in some embodiments the oxygenator 240 also includes one or more porous hollow fibers 270. The one or more porous hollow fibers 270 can be arranged within the oxygenator 240 relative to other portions of the oxygenator 240 as described above in reference to oxygenator 220.

In the depicted embodiment, the one or more porous hollow fibers 270 are wound around the flow distribution element 260. In particular, in the depicted embodiment the one or more porous hollow fibers 270 are wound around the flow distribution element 260 in a crisscrossing pattern. Such a crisscrossing pattern can be a helical pattern. In some embodiments, the wound-density of the one or more porous hollow fibers 270 at the end portions of flow distribution element 260 can be increased as compared to the wound-density of the one or more porous hollow fibers 270 internal from the end portions. Any suitable winding pattern (e.g., pitch, angle, number of wraps, spacing between wraps, and the like) can be used. Any number of filaments (individual hollow fibers) can be used. For example, without limitation, in some cases one filament, two filaments, four filaments, eight filaments, sixteen filaments, thirty-two filaments (or any other suitable number of filaments) can be used (and wound in a desired pattern).

When a crisscrossing pattern is used (e.g., as exemplified without limitation in FIG. 7), a cross-communication between filaments of the one or more porous hollow fibers 270 may be advantageously created in some cases. That is, the intersections of microporous fibers can create a gas communication bridge that can allow gas (e.g., air) to transfer not only along the longitudinal direction of the fiber, but the radial direction (between adjacent fibers). This communication can be very useful for venting the one or more porous hollow fibers 270 from the blood path to atmosphere. Instead of all fibers needing to vent out of the oxygenator 240, a reduced number of the one or more porous hollow fibers 270 can be used to exhaust trapped air. This attribute can also help with manufacturability in some cases.

In some embodiments, the one or more porous hollow fibers 270 can be disposed within the oxygenator 240 in a non-crossing pattern. In some such embodiments, the longitudinal axes of the one or more porous hollow fibers 270 can be parallel to the central longitudinal axis of the oxygenator 240. In some such embodiments, the longitudinal axes of the one or more porous hollow fibers 270 can oriented at a non-zero angle (e.g., between about 0°-10°, or between about 5°-15°, or between about 10°-20°, or between about 15°-25°, or between about 20°-30°, and so on) relative to the central longitudinal axis of the oxygenator 240. In some embodiments, the one or more porous hollow fibers 270 can be a mat of hollow fibers. One or more layers of such a mat of hollow fibers can be used.

In some embodiments, the one or more porous hollow fibers 270 can be used for gas transfer purposes such as, but not limited to, oxygenation of blood and/or removal of carbon dioxide from blood.

FIG. 8 is a photograph of an end portion of an extracorporeal oxygenator 300 (and integrated heat exchanger) that includes an integrated air removal structure, in accordance with some embodiments provided herein. The end cap of the oxygenator 300 is not included in the photograph so as to allow for better visualization of the following components of the oxygenator 300.

The oxygenator 300 includes an oxygenator portion 310, a heat exchanger 320, a flow distribution element 330, and one or more porous hollow fibers 340. In the depicted embodiment, notches 332 are included in an end of the flow distribution element 330. In some embodiments, the notches 332 are created (e.g., machined) after the potting process such that open ends of the one or more porous hollow fibers 340 are thereby created to allow for venting of air from the one or more porous hollow fibers 340 to atmosphere.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A blood oxygenator apparatus, comprising:
a housing defining a blood inlet port and a blood outlet port:
a heat exchanger disposed within the housing, the heat exchanger defining an internal space;
a flow distribution element disposed within the internal space;
a membrane oxygenator portion disposed within the housing, the oxygenator portion arranged concentrically around the heat exchanger; and
one or more porous hollow fibers disposed within the internal space,
wherein the flow distribution element defines a space, and
wherein an open end of at least one of the one or more porous hollow fibers aligns with the space to allow for venting of air from the at least one of the one or more porous hollow fibers.

2. The blood oxygenator apparatus of claim 1, wherein the space is positioned to allow for the venting of air from the at least one of the one or more porous hollow fibers to the internal space.

3. The blood oxygenator apparatus of claim 1, wherein the space comprises a notch.

4. The blood oxygenator apparatus of claim 3, wherein the notch is defined in an end of the flow distribution element.

5. The blood oxygenator apparatus of claim 4, wherein the flow distribution element defines a second space, and wherein an open end of at least a second one of the one or more porous hollow fibers aligns with the second space to allow for venting of air from the at least the second one of the one or more porous hollow fibers.

6. The blood oxygenator apparatus of claim 5, wherein the second space comprises a second notch.

7. The blood oxygenator apparatus of claim 6, wherein the second notch is defined in the end of the flow distribution element.

8. The blood oxygenator apparatus of claim 1, wherein the one or more porous hollow fibers extend around the flow distribution element.

9. The blood oxygenator apparatus of claim 8, wherein a wound-density of the one or more porous hollow fibers is higher at end portions of the flow distribution element than in a middle portion of the flow distribution element.

10. The blood oxygenator apparatus of claim 8, wherein a wound-density of the one or more porous hollow fibers is higher at end portions of the flow distribution element than in a middle portion of the flow distribution element.

11. The blood oxygenator apparatus of claim 8, wherein the one or more porous hollow fibers extend around the flow distribution element in a helical pattern.

12. The blood oxygenator apparatus of claim 8, wherein the one or more porous hollow fibers extend around the flow distribution element in a non-crossing pattern.

13. The blood oxygenator apparatus of claim 1, wherein the flow distribution element comprises:
an outer surface having a frustoconical shape extending from a first end to a second end of the flow distribution element; and
one or more ribs on the outer surface.

14. The blood oxygenator apparatus of claim 13, wherein the one or more porous hollow fibers wrap around the outer surface and the one or more ribs.

15. The blood oxygenator apparatus of claim 13, wherein a region within the frustoconical shape is communicative to an ambient space around the blood oxygenator apparatus.

16. The blood oxygenator apparatus of claim 13, wherein the one or more ribs comprise: (i) long ribs that extend a full length of the outer surface and (ii) short ribs that extend a partial length of the outer surface.

17. The blood oxygenator apparatus of claim 16, wherein the short and long ribs alternate in positions around a circumference of the outer surface.

18. The blood oxygenator apparatus of claim 1, wherein the flow distribution element is configured to facilitate a substantially uniform radial flow distribution of blood entering the heat exchanger.

19. The blood oxygenator apparatus of claim 1, wherein pores of the one or more porous hollow fibers allow air to enter an inside of the one or more porous hollow fibers while preventing liquid from entering the inside of the one or more porous hollow fibers.

* * * * *